US008920496B2

(12) United States Patent
Abel et al.

(10) Patent No.: US 8,920,496 B2
(45) Date of Patent: Dec. 30, 2014

(54) OSSICULAR REPLACEMENT PROSTHESIS

(75) Inventors: Eric William Abel, Dundee (GB); Frank Abraham, Dundee (GB)

(73) Assignee: Sentient Medical Limited, Dundee (GB)

( * ) Notice: Subject to any disclaimer, the term of this patent is extended or adjusted under 35 U.S.C. 154(b) by 1045 days.

(21) Appl. No.: 12/529,461

(22) PCT Filed: Mar. 3, 2008

(86) PCT No.: PCT/GB2008/050147
§ 371 (c)(1),
(2), (4) Date: Jan. 21, 2011

(87) PCT Pub. No.: WO2008/107716
PCT Pub. Date: Sep. 12, 2008

(65) Prior Publication Data
US 2011/0106254 A1 May 5, 2011

(30) Foreign Application Priority Data

Mar. 3, 2007 (GB) .................................. 0704125.4

(51) Int. Cl.
*A61F 2/18* (2006.01)
(52) U.S. Cl.
CPC ............. *A61F 2/18* (2013.01); *A61F 2002/183* (2013.01)
USPC ........................................................ 623/10
(58) Field of Classification Search
CPC ...... A61F 2/18; A61F 2002/183; H04R 25/00
USPC .............................................. 623/10; 600/25
See application file for complete search history.

(56) References Cited

U.S. PATENT DOCUMENTS 2,394,569 A 2/1946 Strommen
3,277,433 A 10/1966 Toulis
(Continued)

FOREIGN PATENT DOCUMENTS

CN 1922402 A 2/2007
CN 1937970 A 3/2007
(Continued)

OTHER PUBLICATIONS

"Design considerations for length variable prostheses: finite element model simulations" by Matthias Bornitz et al.; Middle ear Mechanics in Research and Otology, World Scientific Press 2003.
(Continued)

*Primary Examiner* — Andrew Iwamaye
(74) *Attorney, Agent, or Firm* — Studebaker & Brackett PC

(57) ABSTRACT

An ossicular replacement prosthesis (ORP) (10) for coupling a first point to a second point in the middle ear of a patient, to replace all or part of the ossicular chain. The ORP includes a coupling having a variable configuration for accounting for pressure differentials. The coupling includes a fluid filled chamber (28, 14) having two relatively moveable portions (12, 22) for varying the configuration of the coupling. The coupling further includes unsealed portion constituting leak portion and flowpath portion for permitting displacement of the fluid (30). The relative movement of the relatively moveable portions is controlled by the movement of the fluid in said chamber. The chamber is configured to restrict the movement of the fluid such that relative movement of the moveable portions is permitted in response to quasi-static changes in pressure, and is substantially prevented in response to vibrational changes corresponding to sound frequencies.

12 Claims, 5 Drawing Sheets

(56) References Cited

U.S. PATENT DOCUMENTS

| | | | |
|---|---|---|---|
| 3,594,514 A | 7/1971 | Wingrove | |
| 3,710,399 A | 1/1973 | Hurst | |
| 3,764,748 A | 10/1973 | Branch et al. | |
| 4,118,599 A | 10/1978 | Iwahara et al. | |
| 4,139,728 A | 2/1979 | Haramoto et al. | |
| 4,219,696 A | 8/1980 | Kogure et al. | |
| 4,601,723 A | 7/1986 | McGrew | |
| 4,624,672 A | 11/1986 | Lenkauskas | |
| 4,729,366 A | 3/1988 | Schaefer | |
| 4,759,070 A | 7/1988 | Voroba et al. | |
| 4,774,515 A | 9/1988 | Gehring | |
| 4,809,708 A | 3/1989 | Geisler et al. | |
| 4,845,688 A | 7/1989 | Butler | |
| 4,901,353 A | 2/1990 | Widin | |
| 4,957,478 A | 9/1990 | Maniglia | |
| 4,957,507 A | 9/1990 | Lenkauskas | |
| 5,015,225 A | 5/1991 | Hough et al. | |
| 5,173,944 A | 12/1992 | Begault | |
| 5,233,665 A | 8/1993 | Vaughn et al. | |
| 5,279,292 A | 1/1994 | Baumann et al. | |
| 5,303,306 A | 4/1994 | Brillhart et al. | |
| 5,325,436 A | 6/1994 | Soli et al. | |
| 5,434,924 A | 7/1995 | Jampolsky | |
| 5,436,975 A | 7/1995 | Lowe et al. | |
| 5,456,654 A | 10/1995 | Ball | |
| 5,707,338 A | 1/1998 | Adams et al. | |
| 5,729,077 A | 3/1998 | Newnham et al. | |
| 5,825,894 A | 10/1998 | Shennib | |
| 5,879,283 A | 3/1999 | Adams et al. | |
| 5,913,815 A | 6/1999 | Ball et al. | |
| 5,984,859 A | 11/1999 | Lesinski | |
| 6,001,129 A | 12/1999 | Bushek et al. | |
| 6,137,889 A | 10/2000 | Shennib et al. | |
| 6,203,571 B1 | 3/2001 | Magnan et al. | |
| 6,261,224 B1 | 7/2001 | Adams et al. | |
| 6,315,710 B1 | 11/2001 | Bushek et al. | |
| 6,325,755 B1 | 12/2001 | Bushek et al. | |
| 6,364,825 B1 | 4/2002 | Kennedy et al. | |
| 6,398,717 B1 | 6/2002 | Leysieffer et al. | |
| 6,482,144 B1 | 11/2002 | Muller | |
| 6,490,881 B1 | 12/2002 | Sinclair et al. | |
| 6,537,199 B1 | 3/2003 | Müller et al. | |
| 6,537,200 B2 | 3/2003 | Leysieffer et al. | |
| 6,554,761 B1 | 4/2003 | Puria et al. | |
| 6,629,922 B1 | 10/2003 | Puria et al. | |
| 6,671,559 B2 | 12/2003 | Goldsmith et al. | |
| 6,717,333 B2 | 4/2004 | Hermle et al. | |
| 6,875,166 B2 | 4/2005 | Kroll et al. | |
| 7,289,639 B2 | 10/2007 | Abel et al. | |
| 8,184,840 B2 * | 5/2012 | Spitaels et al. | 381/326 |
| 2003/0097178 A1 | 5/2003 | Roberson et al. | |
| 2005/0165481 A1 | 7/2005 | Steinhardt et al. | |
| 2007/0021833 A1 | 1/2007 | aWengen et al. | |
| 2008/0065002 A1 | 3/2008 | Lobl et al. | |
| 2008/0107546 A1 | 5/2008 | Falch et al. | |
| 2008/0208337 A1 | 8/2008 | Wengen et al. | |
| 2009/0023976 A1 | 1/2009 | Cho et al. | |
| 2009/0131742 A1 | 5/2009 | Cho et al. | |

FOREIGN PATENT DOCUMENTS

| | | | |
|---|---|---|---|
| DE | 2844979 A1 | 4/1980 | |
| DE | 3508830 A1 | 9/1986 | |
| DE | 29701534 U1 | 3/1997 | |
| DE | 202007017910 U1 | 3/2008 | |
| EP | 0 460 354 A2 | 11/1991 | |
| EP | 1 498 088 A2 | 1/2005 | |
| FR | 2 691 354 A1 | 11/1993 | |
| JP | S60154800 A | 8/1985 | |
| JP | S61-42284 A | 2/1986 | |
| JP | H06-310771 A | 11/1994 | |
| RU | 2 096 027 C1 | 11/1997 | |
| WO | 92 18066 A1 | 10/1992 | |
| WO | 97/23117 A1 | 6/1997 | |
| WO | 03/063542 A2 | 7/2003 | |

OTHER PUBLICATIONS

International Preliminary Report on Patentability and Written Opinion of the International Searching Authority with mailing date of Sep. 17, 2009; International application No. PCT/GB2008/050147.

The Examination Report from New Zealand Intellectual Property Office dated Feb. 21, 2011; Patent Application No. 580213.

The First Notification of Office Action from the State Intellectual Property Office of China dated Oct. 20, 2011; Chinese Patent Application No. 200880014653X with translation.

Australian Patent Examination Report No. 1 issued on Jul. 24, 2012, which corresponds to Australian Patent Application No. 2008222478.

Second Notification of Office Action issued by the State Intellectual Property Office of China on Aug. 24, 2012, which corresponds to Chinese Patent Application No. 200880014635.X.

Japanese Office Action "Notice of Reasons for Rejection" dated Nov. 27, 2012, which corresponds to Japanese Patent Application No. 2009-552280.

The third Notification of Office Action issued by the State Intellectual Property Office of China on Apr. 28, 2013, which corresponds to Chine Patent Application No. 200880014635.X and is related to U.S. Appl. No. 12/529,461 with translation.

European Office Action issued on Aug. 22, 2013, which corresponds to EP08709667.3-1662 and is related to U.S. Appl. No. 11/795,137.

Japanese Office Action issued on Jul. 16, 2013, which corresponds to JP2009-552280 and is related to U.S. Appl. No. 11/795,137; with translation.

Canadian Office Action issued on Jul. 18, 2013, which corresponds to Canadian Patent Application No. 2,724,137 and is related to U.S. Appl. No. 11/795,137.

The Japanese Office Action "Notice of Reason for Rejection" dated Jan. 10, 2012, which corresponds to Japanese Patent Application No. 2007-550843 and is related to U.S. Appl. No. 11/795,137 with translation.

The communication pursuant to Article 94(3) EPC dated Feb. 3, 2009, which corresponds to EP Application No. 06 700 906.8. 2320 and is related to U.S. Appl. No. 11/795,137.

The Russian Office Action "Enquiry" dated Dec. 22, 2009, which corresponds to Russian Patent Application No. 2007131471/14(034299) and is related to U.S. Appl. No. 11/795,137 with translation.

The Canadian Office Action dated Oct. 1, 2012, which corresponds to Canadian Patent Application No. 2,594,761 and is related to U.S. Appl. No. 11/795,137.

The Australian Office Action dated Jan. 25, 2013, which corresponds to Australian Patent Application No. 2008249763 and is related to U.S. Appl. No. 11/795,137.

Japanese Office Action "Notice of Reason for Rejection" with mailing date of Feb. 1, 2011; Japanese Patent Application No. 2007-550843 with translation.

Australian Office Action dated Sep. 1, 2010; Patent Application No. 2006205655.

International Search Report dated Mar. 20, 2006 for International Application no. PCT/GB2006/000119.

Written Opinion of the International Search Report for International Application No. PCT/GB2006/000119,. dated Mar. 20, 2006.

Yanagihara et al., "Intraoperative Assessment of Vibrator-Induced Hearing", Advanced Audiology, vol. 4, pp. 124-133, 1988.

Yanagihara et al., "Long-Term Results Using a Piezoelectric Semi-Implanatable Middle Ear Hearing Device: The Rion Device E-Type", Otolaryngologic Clinics of North America, vol. 34, No. 2, pp. 389-400, Apr. 2001.

Zenner et al., Total Implantation of the Implex Tica Hearing Amplifier Implant for High-Frequency Sensorineural Hearing Loss: The Tubingen University Experience, Otolaryngologic Clinics of North America, vol. 34, No. 2, pp. 417-446, Apr. 2001.

(56) References Cited

OTHER PUBLICATIONS

Maassen et al., "Total Implantation of the Active Hearing Implant TICA for Middle Ear Disease: A Temporal Bone Study", Annals of Otolaryngology, Rhinology, and Laryngology, vol. 110, vol. 1, pp. 912-916, Oct. 2001.

Hough et al., Middle Ear Electromagnetic Semi-Implantable Hearing Device: Results of the Phase II SUNDTEC Direct System Clinical Trial., Otology & Neurotology, Inc., vol. 23, No. 6, pp. 895-903, Nov. 2002.

Shih et al., "Scaling Analysis for the Axial Displacement and Pressure of Flextensional Transducers", Journal of American Ceramic Society, vol. 80, No. 5, pp. 1073-1078, 1997.

Gan et al., "Mass Loading on the Ossicles and Middle Ear Function", Annals of Otolaryngology, Rhinology, and Laryngology, vol. 110, No. 5(Pt.1),pp. 478-485, May 2001.

Dogan et al., "Composite Piezoelectric Transducer with Truncated Conical Endcaps 'Cymbal", IEEE Transactions on Ultrasonics, Ferroelectrics, and Frequency Control, vol. 44, No. 3, pp. 597-605, May 1997.

Brigham et al., "Present Status in the Design of Flextensional Underwater Acoustic Transducers", Summary of paper in Acoustical Society of America 77th Meeting, vol. 46, No. 1(Pt.1), p. 92, 1969.

Newnham et al., "Flextensional Moonie Actuators", 1993 Ultrasonics Symposium, pp. 509-513, 1993.

Hough et al., "Semi-Implantable Electromagnetic Middle Ear Hearing Device for Moderate to Severe Sensorineural Hearing Loss", Otolaryngologic Clinics of North America, vol. 34, No. 2, pp. 401-416, Apr. 2002.

An Office Action issued by the Government of INDIA Patent Office on Jun. 24, 2013, which corresponds to Indian Patent Application No. 1102/MUMNP/2007 and is related to U.S. Appl. No. 11/795,137.

"First Notification of Office Action" issued by the State Intellectual Property Office of China on Jan. 28, 2014, which corresponds to Chinese Patent Application No. 201080032713.6 and is related to U.S. Appl. No. 12/529,461; with English language translation.

"First Notification of Office Action" issued by the State Intellectual Property Office of China on Feb. 27, 2014, which corresponds to Chinese Patent Application No. 201080032735.2 and is related to U.S. Appl. No. 12/529,461; with English language translation.

An Office Action issued by the Canadian Patent Office on Dec. 13, 2013, which corresponds to Canadian Patent Application No. 2,717,361 and is related to U.S. Appl. No. 12/529,461.

An Office Action; "Advisory Action Before the Filing of an Appeal Brief," issued by U.S. Patent Office on Feb. 11, 2014, which corresponds to U.S. Appl. No. 12/599,530.

The forth Notification of Office Action issued by the State Intellectual Property Office of China on Nov. 22, 2013, which corresponds to Chinese Patent Application No. 200880014635.X and is related to U.S. Appl. No. 12/529,461; with English language translation.

Leiner, et al.; "A Pathway for Information Transmission to the Inner Ear Application to Cochlear Implants"; ASAIO Journal 1992; 38: pp. M253-M256.

An Office Action issued by the Canadian Intellectual Property Office on Aug. 22, 2013, which corresponds to Canadian Patent Application no. 2,594,761 and is related to U.S. Appl. No. 12/529,461.

Notice of Allowance issued by the Australian Patent Office on Aug. 16, 2013, which corresponds to Australian Patent Application No. 2008222478 and is related to U.S. Appl. No. 12/529,461.

* cited by examiner

OSSICULAR REPLACEMENT PROSTHESIS

FIELD OF THE INVENTION

The present invention relates to an ossicular replacement prosthesis, and in particular, but not exclusively, to an ossicular replacement prosthesis incorporating a Newtonian or non-Newtonian fluid system.

BACKGROUND TO THE INVENTION

An ossicular replacement prosthesis (ORP) is a structure that replaces part or all of one or more of the three bones of the ossicular chain of the human middle ear. A schematic representation of the ossicular chain is shown in FIG. 1. The ossicular chain, generally represented by reference numeral 1, comprises three connected bones, called auditory ossicles, which extend across the middle ear from the tympanic membrane (eardrum) 3, to the oval window (not shown). The bones include the malleus 5, which has landmark portions known as the neck or handle (more strictly the manubrium) 7, and the head 9; the incus 11, which includes a body portion 13; and the stapes 15. These bones are also known colloquially and respectively as the hammer, anvil and stirrup. The malleus 5, engages the eardrum 3, and is articulated to the incus 11, via the incudomalleal joint (IMJ) 17. The incus 11, in turn, is articulated with the stapes 15, via the incudostapedial joint (ISJ) 19, and the footplate 21, of the stapes 15, engages the oval window (not shown). Sound induced vibration of the eardrum 3, is thus transmitted across the ossicular chain 1, to the cochlea (not shown) of the inner ear.

ORPs are used in ossicular chain reconstruction in cases where the normal process of sound conduction from the eardrum to the inner ear is impeded by a failure of part or all of the ossicular chain to transmit the vibrations generated from sound arriving at the eardrum. The ORP provides a sound conduction bridge across the gap created when the dysfunctional parts of the ossicular chain are removed.

An ORP is implanted using a surgical procedure in which the middle ear is usually approached via the external ear canal and an incision is made around the eardrum which is then reflected to provide access to the middle ear cavity.

ORPs are classified by some worker in this field as Total ORPs (TORPs) and Partial ORPs (PORPs), the former spanning the complete ossicular chain from the eardrum to the oval window and the latter spanning part of the ossicular chain. There are also acronyms for other types of PORP. For example a PORP that replaces an incus (an incus replacement prosthesis) may be referred to as an IRP. In addition, special prostheses for treating otosclerosis are used in stapedectomy surgery. However, the term ORP as used herein is intended to refer generally to any device which is used to replace part or all of the ossicular chain.

An ORP must possess a number of properties in order to function effectively. For example, those parts which are exposed to the internal environment of the body and those in direct contact with body tissue must be biocompatible and chemically stable. Additionally, an ORP should be rigid enough and have sufficiently low mechanical damping to transmit acoustically derived vibrations with minimal or low loss of signal. Furthermore, an ORP should not impart any more loading to the ossicular chain by virtue of its mass than is absolutely necessary or clinically acceptable. During its lifetime, which may be many years, an ORP may be subjected to billions of vibrating cycles in the audio frequency range and must, therefore, maintain its structure and function with minimal deterioration.

Existing ORPs are manufactured in a wide range of shapes and sizes, and are designed to span the gap left after the excision of a portion or all of the ossicular chain. ORPs have a wide range of end-fittings constituting attachment means for attachment to the bones at each side of the gap. There are various means used in ORPs for attachment to the ossicular chain, including, non-exhaustively, wires, spring clips and other components which may be crimped into place. These attachment means form part of the prosthesis and usually rely on a lock or a friction fit between the prosthesis and the tissue. Cements constitute generally less-preferred attachment means and very few of them are approved for use in the middle ear by regulatory bodies, such as the Food and Drug Administration in the USA. Bioactive materials, such as calcium hydroxyapatite (syn. hydroxylapatite), form a chemical bond between bone and the implant and may be used alone or in a hybrid form with another means of attachment.

Some ORPs are offered in a considerable range of sizes whereas others are presented in only a few sizes or in a single size which can be modified to fit the patient intraoperatively by reshaping or by size reduction (cutting down). However, intraoperative modification may be difficult and time consuming.

In addition to transforming sound into a suitable form of vibration to activate the cochlea in the inner ear, the middle ear also has means for compensating for large static, or quasistatic, variations in atmospheric pressure (alternatively herein termed ambient pressure) which could otherwise cause sufficiently large and potentially damaging displacements of the ossicular chain.

Examples of commonly experienced effects of ambient pressure variations include passing into and out of a railway tunnel whilst on a train running at high speed, travelling in an aircraft during ascent and descent, underwater diving and nose-blowing. Compensation for ambient pressure changes is achieved by various means including the ability of the IMJ (17, in FIG. 1) to move in such a manner that high levels of deflection of the eardrum passed to the malleus are not transmitted via the incus to the stapes.

Implantation of all TORPs and most PORPs involves removing the incus, thereby destroying the ISJ and IMJ, which, in turn, results in the loss of the motion-limiting compensation mechanism. Accordingly, an ORP which provides effective means for preventing large changes in atmospheric pressure leading to excessive motion at the stapes footplate (21 in FIG. 1) is desirable. For example, a spring element forming part of an ORP could deflect under a force generated by a static pressure and so provide such compensating means. Examples of ORPs that employ spring elements are disclosed in U.S. Pat. Nos. 6,203,571 B1, 4,957,507, 4,624,672, WO 92/18066 and FR 2691354. However, the use of a spring element is not now generally regarded in the art as an optimal solution. For example, it has been pointed out by Bornitz et al (Design Considerations For Length Variable Prostheses: Finite Element Model Simulation, Middle Ear Mechanics in Research and Otology, eds. K. Gyo and H. Wada, World Scientific Press, 2003) that other means of adjustment to the length of an ORP would be desirable. Their proposals include a spring element, a damping element, a friction element and a buckling element. They conclude that a combined spring and damping element would be the best option for this purpose, although they concede that no realisation of such a device is yet known.

It is among the objects of embodiments of the present invention to seek to address these and other limitations in the prior art.

SUMMARY OF THE INVENTION

According to a first aspect of the present invention, there is provided an ossicular replacement prosthesis comprising a deformable coupling provided with first and second attachment points, being together configured to provide coupling means between anatomical, prosthetic or otherwise artificial components, or any suitable combination thereof disposed within the auditory system of a human patient such that when the deformable coupling is exposed to sound induced vibrations, for example originating from the tympanic membrane (eardrum), these vibrations may be transmitted across the coupling means with minimal acoustic damping or attenuation.

In one embodiment of the present invention, presented as a TORP, the deformable coupling may be configured to replace all three ossicles of the ossicular chain so as to extend between the tympanic membrane and the oval window. In another embodiment of the present invention presented as a PORP, the deformable coupling may be configured to replace all or part of one or more (but less than the totality of all three) ossicles so as to bridge a gap in the ossicular chain.

Preferably, the deformable coupling is selectively deformable and additionally is configured to deform in response to variations in local ambient pressure. Beneficially, deformation of the coupling in this manner permits relative movement between the first and second attachment points.

It is well known that sound propagates as waves of alternating pressures of a dynamic or transient nature which deviate from the local ambient pressure. These dynamic sound pressure variations or acoustical pressure variations are detected by the auditory system and conducted across the middle ear as sound induced vibrations. Sound pressure variations generally impose minimal forces on the auditory system. However, changes in ambient pressure, which are generally of a static or quasistatic nature, can impart forces to the eardrum and ossicular chain which may be up to 10,000 times or more larger with the potential to cause much larger and possibly damaging deflections of the ossicular chain.

Accordingly, the present invention advantageously permits sound induced vibrations to be transmitted across the deformable coupling with minimal acoustic damping or attenuation, while simultaneously permitting the coupling to deform in response to local ambient (high) pressure changes. In this way, the ORP of the present invention may operate as an effective acoustic transmission or conduction component while changes in ambient pressure will be damped or absorbed such that the effects of said ambient pressure changes will not be transmitted across the coupling, ultimately protecting the inner ear and other auditory system components of the patient.

The deformable coupling of the ORP may permit relative rectilinear motion of the first and second attachment points. Alternatively, or additionally, the deformable coupling may be configured to be deformed to permit rotational motion between the first and second attachment points. Rectilinear and rotational deformation of the coupling may also facilitate the process of fixation of the first and second attachment points to components within the auditory system of the patient during implantation, thus eliminating or minimising the need for intraoperative adaptation.

Preferably, the deformable coupling is of variable stiffness and more preferably, its stiffness varies in response to an external stimulant or condition, such that, for instance, it decreases in response to an increased applied load or force associated with ambient pressure increase.

Preferably, the deformable coupling is configured to become sufficiently stiff or rigid when exposed to a dynamic load or force associated with sound pressure variations in the audio frequency range, such that in use it may transmit sound induced vibrations with minimal acoustic damping or attenuation.

Advantageously, the deformable coupling may comprise means for exerting a pre-load between the first and second attachment points, which pre-load may act to induce tension or compression within the auditory system of the patient thereby enhancing effectiveness of the ORP. The pre-load may be provided by means of an elastic material covering all or part or the ORP or other elastic means within the ORP.

According to a second aspect of the present invention, the deformable coupling contains a fluid selected in accordance with preferential hydrodynamic and other properties to provide a desirable stiffening response of the coupling when loading occurs between the first and second attachment points. The fluid may a be a Newtonian fluid or it may be a non-Newtonian fluid, such as a dilatant or shear-stiffening fluid. Non-Newtonian fluids exhibit nonlinear stress velocity behaviour which results in velocity/frequency dependent viscosity behaviour. Shear-stiffening fluids increase in viscosity with increasing shear rate at a given temperature and pressure; the shear rate increasing with velocity or frequency of motion so that the dilatant fluid of the ORP of the present invention preferentially exhibits an increase in stiffness as the input frequency increases.

Alternatively, the non-Newtonian fluid may comprise a thixotropic fluid (also known as a shear-thinning, or pseudo-plastic fluid), which exhibits a decrease in viscosity with increasing shear rate at a given temperature and pressure. Such fluids appear to be rigid at rest and subsequently fluidise when sheared. Accordingly, when the small forces caused by acoustical sound waves are applied to the prosthesis of the present invention they will be of insufficient magnitude to shear the fluid which remains substantially rigid and capable of transmitting sound derived vibrations.

In marked contradistinction, loads associated with ambient pressure changes have sufficient magnitude to shear the thixotropic fluid so much that its viscosity is altered and it becomes more fluid allowing the deformable coupling to deform in response to the load introduced by larger ambient pressure variations which are thereby compensated. Pressure equalisation in response to ambient pressure change events is achieved via the Eustachian tube of the auditory system whereafter a thixotropic fluid would become rigid again.

According to a third aspect of the present invention, there is provided an ossicular replacement prosthesis comprising a deformable coupling having first and second attachment points configured to be coupled between components within the auditory system of a patient, said deformable coupling comprising a fluid-filled container and having a flowpath, wherein interaction of fluid within the flowpath in response to a force applied on the deformable coupling permits the first and second attachment points to be substantially fixed relative to each other when the deformable coupling is exposed to sound induced vibrations.

Preferably, the flowpath opens into a cavity formed within or adjacent to the container, wherein the flowpath is of a smaller cross-sectional dimension or capacity than that of the cavity. The cavity may be provided with a rigid or flexible boundary. In use, certain forces applied to the deformable coupling will cause the fluid to be displaced through or along the flowpath.

Small loads derived from acoustical pressures are oscillatory and of short duration and when imparted to the deformable coupling are insufficient to overcome the fluid resistance within the flowpath and will not result in any significant movement of the fluid therethrough. However, forces resulting from static or quasistatic ambient pressure variations, which are generally applied in a single direction and are of relatively extended duration, are sufficient to displace the fluid and thus cause the coupling to deform. This effect may be reinforced by friction forces or mass effects within the coupling.

In one embodiment of the present invention, the deformable coupling may comprise a piston slidably mounted within the container. The piston preferably extends externally to the container. The extending portion may be of the same diameter or effective width as that of the piston or it may have a different dimension. Preferably, a free end of the piston, located external to the container, may be one of the first and second attachment points. In addition, it is preferable that the other of the first and second attachment points is disposed on the container. Accordingly, relative movement of the first and second attachment points may be achieved by corresponding relative movement of the piston within the container. Beneficially, the piston is disposed within the container such that it interfaces with a fluid, preferably but not essentially a non-Newtonian fluid, also located within the container.

Advantageously, the piston may divide the container into first and second cavities, wherein movement of the piston within the container results in a respective and corresponding volume change of the first and second cavities and the movement of fluid from one cavity to the other cavity. Fluid communication may be achieved via ports extending through the piston or, advantageously, via ports in the container. Alternatively, or additionally, fluid communication may be achieved via a passage, which may be annular, disposed between the piston and an inner wall of the container.

Accordingly, the piston and container may advantageously collectively define a fluid damper which exhibits a stiffness characteristic that increases with increasing frequency of motion of the piston relative to the container. This stiffness characteristic may advantageously assist to permit the deformable coupling to become sufficiently stiff when exposed to audio frequency range derived forces, while becoming sufficiently flexible in response to loading from forces derived from the sub-audio range, such as from those pressures exerted on the eardrum of a patient resulting from static or quasistatic changes in ambient air pressure.

Furthermore, advantage may be taken of the combination of stick-slip, the characteristics of the fluid within the container and the geometrical features of the piston and container, whereby the ORP of the present invention will effectively provide high resistance to motion at pressure variations associated with audio frequencies and compliance when subjected to pressures transmitted from the eardrum which might otherwise cause discomfort and even damage to structures of the middle ear and inner ear.

The term Astick-slip@ refers to an occurrence where two surfaces in contact or approximation may move with respect to one another only if the applied force is sufficient to overcome the frictional and surface contact forces that tend to prevent this movement.

Advantageously, where the fluid within the container comprises a dilatant non-Newtonian fluid, movement of the piston in response to an applied static or dynamic force will affect the viscosity and thus the effective stiffness of said dilatant fluid. Accordingly, the stiffness of the fluid damper, defined by the piston and container, will increase with increasing frequency of motion which effect synergistically combines with the effect of the increasing stiffness of the non-Newtonian fluid with increasing frequency. This mutually reinforcing arrangement effectively provides a rapid increase in stiffness with increasing frequency, while permitting the deformable coupling to exhibit sufficiently low stiffness at the frequencies associated with static or quasistatic pressure changes and a sufficiently high stiffness at audio frequencies.

The deformable coupling may incorporate a conduit or connecting portion extending between the first and second cavities of the container. The wall of the container preferably defines first and second ports, said first port adjacent said first cavity and said second port adjacent said second cavity, wherein the conduit extends between said first and second ports. Preferably, the piston is configured to be translated within the container between the ports, such that in use, movement of the piston displaces fluid between the first and second cavities via the connecting portion. The resistance to a fluid movement along the conduits or connecting portion may be provided according to the diameter or cross section of the connecting portion and its length.

According to a fifth aspect of the present invention, there is provided an ORP wherein the deformable coupling may comprise a rotatable element rotatably mounted within the container. The rotatable element is preferably coupled to an axle which extends externally to the container. Preferably, the rotatable element comprises at least one vane mounted on the axle and radially extending therefrom. Advantageously, the first attachment point is provided on or adjacent an end of the axle positioned externally to the container, and the second attachment point is disposed upon the container. Accordingly, rotation of the axle relative to the container will result in relative rotational movement of the first and second attachment points. Advantageously, a flexible cover fixed at the container and circumferentially on the axle prevents any leakage of fluid or fluid vapour from contacting the tissues of the middle ear and isolates the ORP from contamination from tissues and body fluids. The flexibility of the cover is sufficient to allow relative rotational movement of the first and second attachment points and may be made of a material and shape that provides means to exert a pre-load between the first and second attachment points, which pre-load may act to induce tension or compression within the auditory system of the patient thereby enhancing effectiveness of the ORP. The pre-load may be provided by means of an elastic material covering part or all or the ORP or by other elastic means within the ORP.

Beneficially, the at least one vane is disposed within the container and is configured so as to engage and interface with a fluid contained therein. Preferably, but not essentially, the fluid is a non-Newtonian fluid and the vane is configured by, for example holes or ports or the like, provided therein such that in use, fluid is permitted to pass therethrough. Alternatively, or additionally, the vanes may be disposed within the container and arranged so as to permit fluid to pass over said vanes. For example, the vanes may be so disposed such that the tips thereof or both the tips and the edges thereof may approximate the inner surface of the container so as to define a gap.

Accordingly, the vane and container may advantageously collectively define a rotational fluid damper which exhibits a stiffness characteristic that increases with increasing frequency of motion of the vane relative to the container. This stiffness characteristic may advantageously assist to permit the deformable coupling to become sufficiently stiff when exposed to forces derived from acoustical vibrations in the audio frequency range, while becoming sufficiently flexible in response to forces derived from static or quasistatic changes in ambient air pressure.

Advantageously, where the fluid within the container comprises a non-Newtonian fluid, movement of the vanes in response to an applied static or dynamic force will affect the viscosity and thus effective stiffness of said non-Newtonian fluid. Accordingly, the increasing stiffness of the fluid damper defined by the vanes and container with increasing frequency of motion combines with the effect of the increasing stiffness of the non-Newtonian fluid with increasing frequency. Furthermore, as noted above, advantage may be taken of the combination of stick-slip and the resistance to motion of the fluid within the rotational damper.

According to a sixth aspect of the present invention, there is provided an ORP wherein the deformable coupling comprises first and second friction elements coupled together via a friction coupling, wherein the first friction element supports the first attachment point and the second friction element supports the second attachment point. Advantageously, the friction coupling is created by an interference fit between portions of the first and second friction elements. Advantageously, relative movement between the first and second elements is achievable when said elements are exposed to a force sufficient to overcome the stick-slip effect or static friction of the interference fit. Advantageously, the friction elements collectively operate to provide a stick-slip effect with a high resistance to the small forces associated with and derived from normal audio frequencies such that these forces are too low to overcome the static friction of the interference fit, resulting in an effective rigid coupling, while the higher forces arising from quasistatic pressures on the eardrum overcome the static friction of the interference connection and allow relative movement of the elements.

BRIEF DESCRIPTION OF THE DRAWINGS

These and other aspects of the present invention will now be described, by way of example only, with reference to the accompanying drawings, in which.

DETAILED DESCRIPTION OF THE DRAWINGS

In the following description FIGS. 2-11, refer to preferred embodiments of an ORP having the respective general designations 10, 100, 200, 300, 400, 500, 600 and 700.

Figure 1:
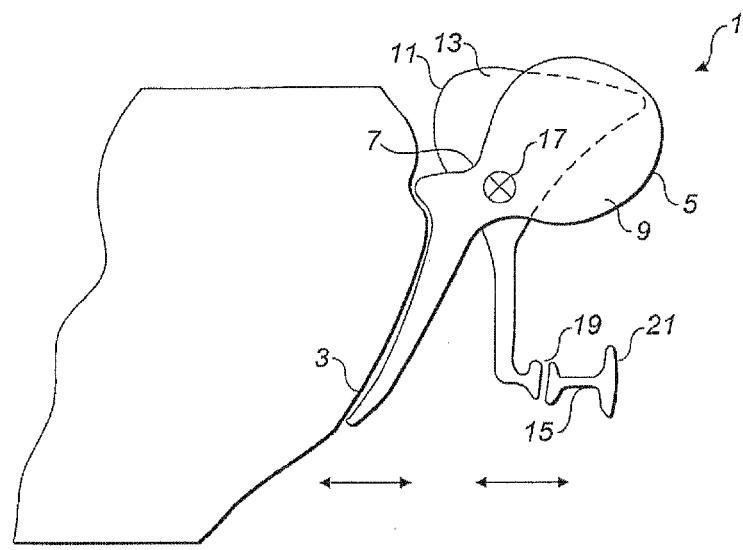
FIG. 1, is a diagrammatic representation of the human ossicular chain and component structures thereof.
Figure 2:
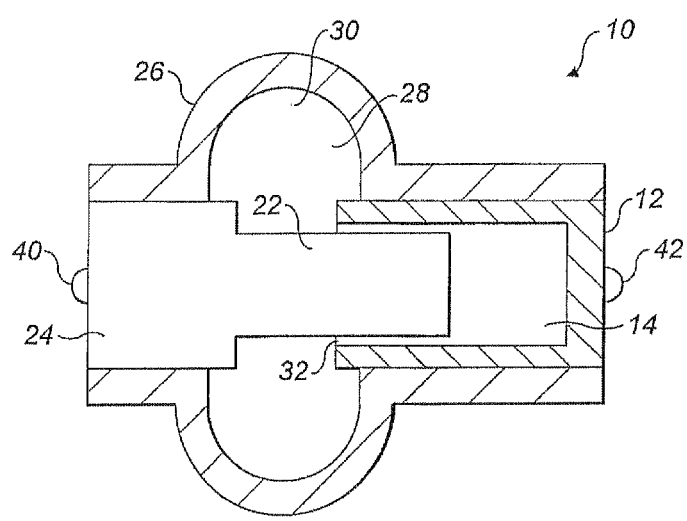
FIG. 2, is a diagrammatic representation of a first preferred embodiment of an ORP according to the present invention in which the principle of operation depends upon a construct which allows leakage of fluid past a piston in a bore.

A first preferred embodiment of the present invention is shown in FIG. 2, of the drawings in which ORP 10, comprises a container 12, having a single bore 14, within which is slidably mounted a piston 22. A flexible cover 26, is secured to container 12, and to a free end 24, of piston 22, so as to enclose a chamber 28, filled with fluid 30, which is preferably a non-Newtonian dilatant fluid. Piston 22, defines an annular clearance 32, between piston 22, and bore 14, such that fluid 30, may be displaced through annular clearance 32, between bore 14, and chamber 28. Accordingly, the resistance of fluid 30, across annular clearance 32, in response to the type of loading applied on ORP 10, will affect changes to the effective stiffness thereof. It is to be noted that this construct and operational mode of ORP 10, obviates the need for fluid-sealing means between piston 22, and container 12. Indeed, the fundamental principal of operation requires that fluid 30, leaks past piston 22. Flexible cover 26, ensures integrity of fluid 30, in chamber 28. This configuration simplifies the structure of the ORP. Moreover, this configuration eliminates the risk of leakage of fluid and the ingress of biological matter, seen with standard piston to cylinder seals.

ORP 10, has first and second attachment points 40; 42, for non-releasable attachment to suitable sites on anatomical structures and prosthetic or otherwise artificial components of the auditory system. Attachment points 40; 42, may be secured to components of the auditory system via wires, crimping means, clips, cement, glue, friction couplings or the like, or any suitable combination of fixing means (none of these are illustrated).

Figure 3:
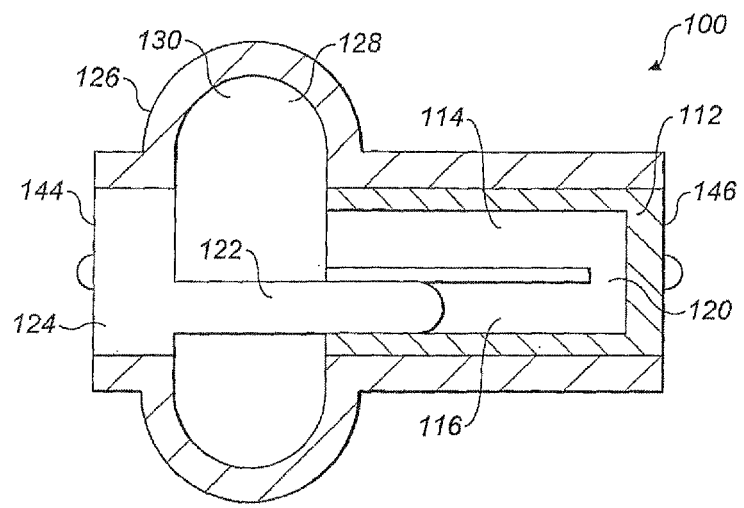
FIG. 3, is a diagrammatic representation of a second preferred embodiment of an ORP according to the present invention in which the principle of operation depends upon provision of a construct which allows fluid and a plurality of chambers to cooperate as a mechanical damper.

In FIG. 3, there is shown a diagrammatic representation of a second preferred embodiment of the present invention wherein an ORP, generally identified by reference numeral 100, comprises a container 112, having first and second bores 114; 116, in fluid communication via a connecting portion 120. A piston 122, is slidably mounted within second bore 116. A flexible cover 126, is mounted over or secured to container 112, and is coupled to a free end 124, of piston 122. Flexible cover 126, encloses a chamber 128, within which is contained a fluid 130, which preferably may be a non-Newtonian dilatant fluid.

Flexible cover 126, may be formed of an elastomeric material, such as silicone. Fluid 130, is free to be displaced, depending on the relative positioning of container 112, and piston 122. This embodiment is a construct having the fundamental properties of a mechanical damper, wherein the damping effect in ORP 100, increases with increasing frequency of input frequencies in the audible spectrum which produce small loading pressures of very short duration and which may further contribute to the stiffening derived from the intrinsic properties of the non-Newtonian dilatant fluid 130.

ORP 100, is configured to span a gap in an ossicular chain of a patient, with piston head 144, and an end 146, of container 112, being secured to appropriate anatomical or prosthetic components within a patient's middle ear cavity. Accordingly, a load applied to ORP 100, will act so as to cause, or tend to cause, relative movement between piston 122, and container 112. In use, loads associated with sound pressure variations, which are low in magnitude and oscillatory in nature, result in substantially no movement of piston 122, relative to container 112, by virtue of the resistance to motion of the fluid within bores 114; 116. Accordingly, ORP 100, effectively becomes stiff when exposed to loading in the audio frequency range and as such permits sound induced vibrations to be transmitted across it.

However, when ORP 100, is exposed to loads associated with variations in ambient pressures, which are large relative to those associated with sound pressure variations, and which, in addition, are applied generally in a single direction, ORP 100, is compliant (becomes deformable) because such loads are sufficient to overcome the resistance to motion of fluid 130, which is displaced along bores 114; 116.

Figure 4:
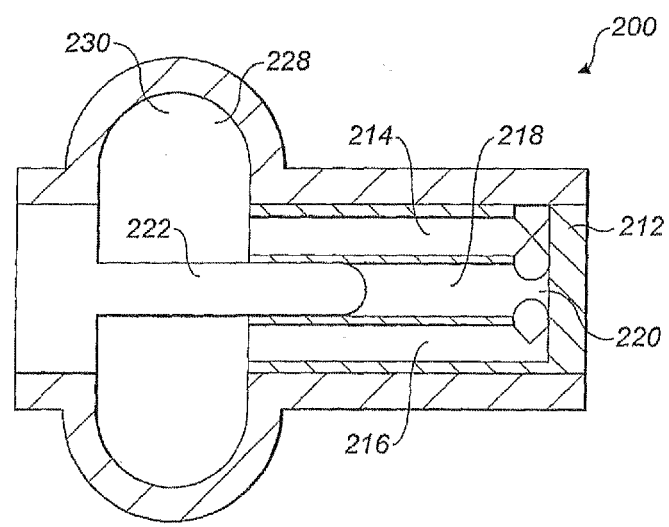
FIG. 4, is a diagrammatic representation of a further preferred embodiment of an ORP according to the present invention in which is provided a further mechanical damper.

Turning now to FIG. 4, there is illustrated a further preferred embodiment of an ORP according to the present invention and generally identified by reference numeral 200. ORP 200, is also a construct having the fundamental properties of a mechanical damper and is substantially similar in many respects to the arrangement of ORP 100, immediately hereinbefore described with reference to FIG. 3. In this embodiment, ORP 200, comprises a container 212, which incorporates three bores 214, 216, 218, which are in fluid communication with each other via a suitable connecting portion 220. A piston 222, is located within middle bore 218, and in use causes fluid 230, which is preferably although not exclusively a non-Newtonian fluid, to be displaced along outer bores 214, 218, which are in communication with chamber 228. The operation of ORP 200 is substantially similar to that shown in FIG. 3.

Figure 12:
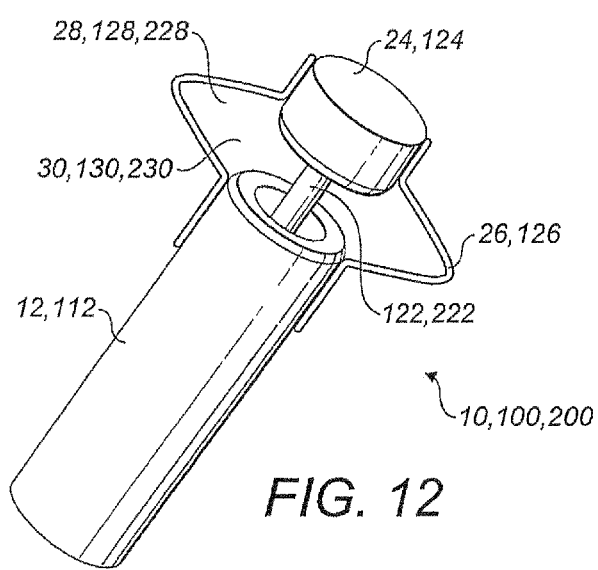
FIG. 12 is an alternative view of the ORP of FIG. 2, 3 or 4.

FIG. 12 is an alternative view of the ORP of FIG. 2, 3 or 4, which shows the flexible cover 26/126 that contains the fluid which leaks past the piston 122/222.

In the embodiments illustrated with reference to FIGS. 2-4, the movement resistance function of the respective ORPs 10; 100; 200, may be further reinforced by contact friction forces and inertial effects. Furthermore, these embodiments may be configured and positioned within the ossicular chain of a patient in a variety of ways, such as those immediately hereinafter described with reference to FIGS. 5-8.

Figure 5:
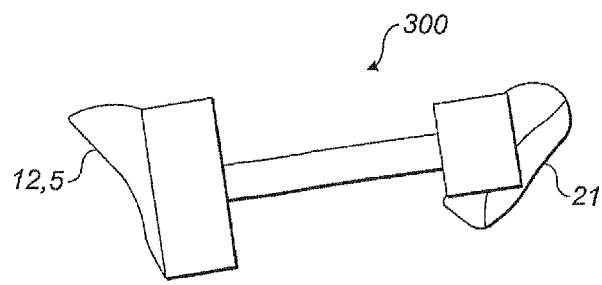
FIGS. 5 to 8, are diagrammatic representations of different configurations of the embodiments of FIGS. 2-4.

In FIG. 5, an ORP, generally identified by reference numeral 300, extends between the eardrum 12, or a residual part (not separately numbered) of the malleus 5, and the footplate 21, of the stapes 15, such that ORP 300, functions as a total ORP (usually referred to by those skilled in the art as a TORP).

Figure 6:
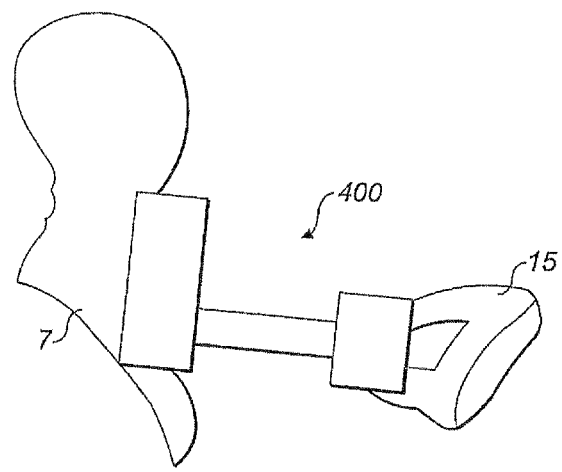

In FIG. 6, an ORP, in this case identified by reference numeral 400, extends between the manubrium 7, of the malleus 5, and the stapes 15. In this case, ORP 400, is a partial ORP (usually referred to by those skilled in the art as a PORP).

Figure 7:
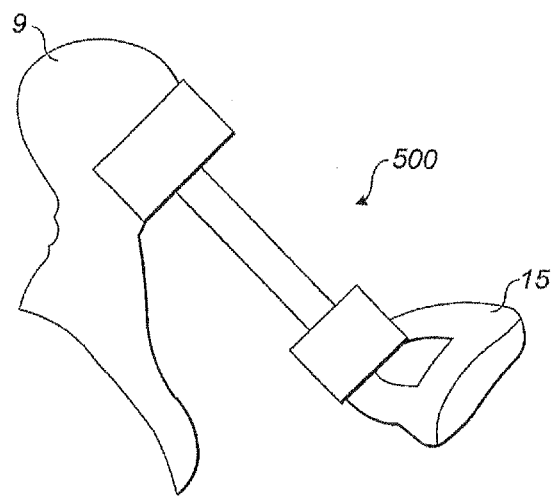

In FIG. 7, an alternative PORP, identified by reference numeral 500, is shown extending between the head 9, of the malleus 5, and the stapes 15.

Figure 8:
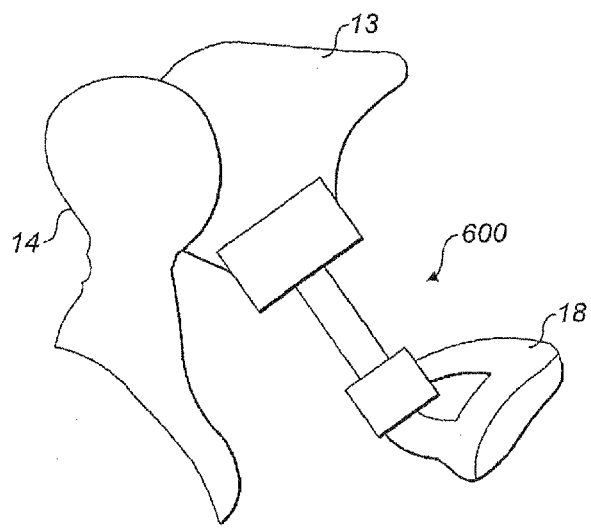

A further alternative PORP, 600, is shown in FIG. 8, extending between the body 13, of the incus 11, and the stapes 15.

Figure 9:
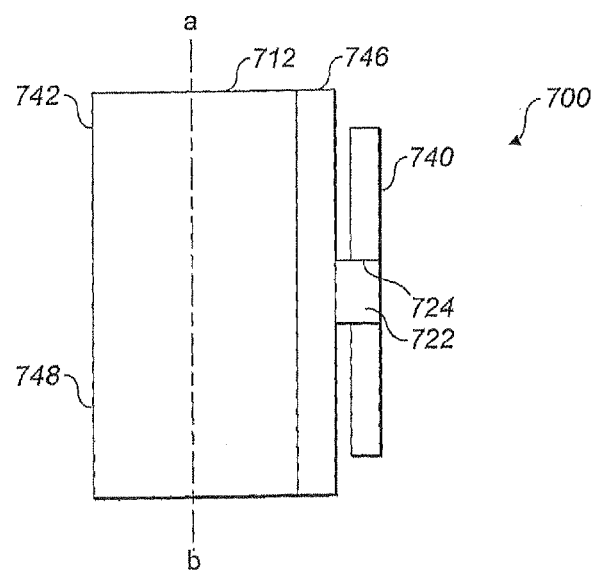
FIG. 9, is a diagrammatic representation of a further preferred embodiment of an ORP according to the present invention in which a deformable coupling deforms by rotation, wherein fluid, a container and at least one vane cooperate to function as a rotational fluid damper.

Reference is now made to FIG. 9, of the drawings in which there is shown a side view of an ORP, generally identified by reference numeral 700, which is a further preferred embodiment of the present invention. ORP 700, comprises a container 712, closed by first and second end caps 746; 748. An axle 722, is rotatably mounted within container 712, into which it extends through first end cap 746. A first attachment point 740, is secured to a free end 724, of axle 722, located externally to container 712, and a second attachment point 742, is positioned on container 712. Attachment points 740; 742, provide securing means for securing ORP 700, between components within the auditory system of a patient. Accordingly, relative rotational motion of axle 722, and container 712, results in corresponding relative rotational motion of first and second attachment points 740; 742.

Figure 10:
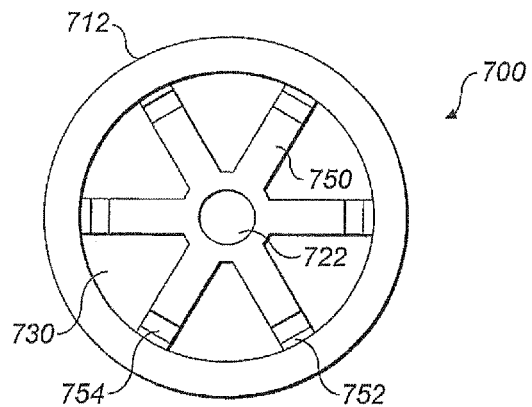
FIG. 10, is a cross-sectional view of the ORP of FIG. 9, through line a-b.

Turning to FIG. 10, there is shown a cross-sectional view of ORP 700, through line a-b, in FIG. 9. Container 712, is filled with fluid 730, which may be a Newtonian or a non-Newtonian fluid. Axle 722, carries a plurality of circumferentially distributed and radially extending vanes 750, which are configured to be rotated with axle 722. In this embodiment, vanes 750, are each provided with a port or hole 754, adjacent to tip 752, thereof, whereby each hole 754, permits the passage of fluid 730, therethrough upon rotation of vanes 750, relative to container 712. Accordingly, vanes 750, container 712, and fluid 730, collectively define a rotational fluid damper which exhibits a stiffness characteristic which increases with increasing frequency of motion of the vane relative to the container. Where a non-Newtonian fluid is utilised, movement of the vanes in response to an applied static or dynamic force will affect the viscosity and thus the effective stiffness of the fluid damper which increases with increasing frequency of motion.

In certain embodiments a seal between axle 722 and container 712 may be provided.

Furthermore, advantage may be taken of the combination of stick-slip and the resistance to motion of the fluid within the damper through selection of a suitable fluid and careful design of the geometrical features of the damper components. By these means, the rotational fluid damper mechanism of this embodiment can provide high resistance to motion at audio frequencies but compliance when subjected to quasistatic atmospheric pressure changes.

Figure 11:
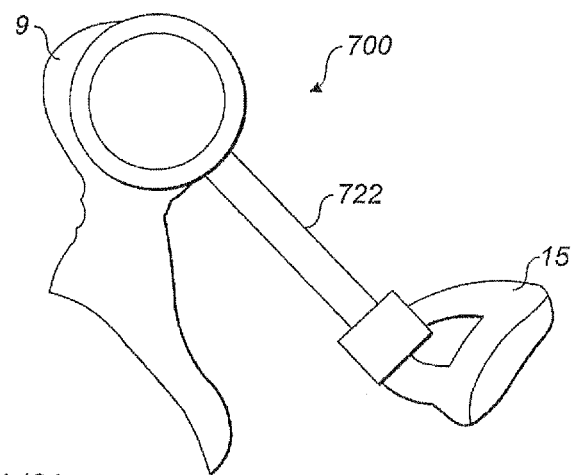
FIG. 11, is a view of the ORP illustrated in FIGS. 9 and 10, configured as a PORP and in position within a human patient.

FIG. 11, is a view of ORP 700, in position and used as a PORP, in which ORP 700, is secured to the head 9, of the malleus 7. An extension arm 722, may extend between ORP 700, and the stapes 15, in order to bridge the gap in the ossicular chain. Extension arm 722, may comprise a rigid structure. Alternatively, or additionally, extension arm 722, may comprise a linear ORP, such as an ORP hereinbefore described with reference to FIGS. 2-4.

First and second attachment points 740, 742, are mounted on respective opposing first and second end caps 744; 746, of container 712, thereby providing means for securing ORP 700, between components of the auditory system of a patient. First and second attachment points 740; 742, may be secured to anatomical components, prosthetic or otherwise artificial components of the auditory system. Although not shown, attachment points 740; 742, may be secured to components of the auditory system via wires, crimping means, clips, cement, glue, friction couplings or the like, or any suitable combination of fixing means (not illustrated).

Suitably designed ORPs according to the principles of embodiments of the present invention described herein, whether they be TORPs or PORPs (or some other category of ossicular replacement prosthesis), would be capable of providing for movement of approximately ∀ 0.5 mm to 1.0 mm deflection to accommodate the effects of low frequency changes associated with static and quasistatic pressure changes, whilst concomitantly providing a sufficiently rigid structure at audio frequencies to enable adequate transmission of vibrations to satisfy the clinical and consumer requirements of an ORP.

It should be understood that the embodiments described are merely exemplary and that various modifications may be made without departing from the scope of the present invention.

In the present specification, references to sound and sound vibrations are references to vibrations whose frequencies lie between about 20 and 20 000 Hertz, and which thus lie within the range of perception of the human ear. References to static or quasi-static pressure variations refer to pressure which differs from normal ambient pressure by a constant amount, or which varies substantially more slowly than in sound vibrations. For example, slowly varying but high magnitude pressure changes that occur mainly due to changes in atmospheric pressure (but also passing through train tunnels, etc.) and which are substantially below the audio frequency range.

The invention claimed is:

1. An ossicular replacement prosthesis (ORP) for coupling an ossicular bone or an eardrum of a patient to another point in the middle ear of the patient, to replace all or part of the ossicular chain, the ORP comprising:
   a coupling having a variable configuration for accounting for pressure differentials, said coupling comprising a container, a piston, and a cover secured to the container and the piston thereby forming an enclosed chamber, the chamber filled with a fluid, the piston slidably mounted in a bore defined by the container for varying the configuration of the coupling and relative movement of the container and the piston,
   wherein an annular clearance is defined between an outer surface of the piston and an inner surface of the bore of the container for permitting displacement of the fluid within the chamber through said annular clearance, the relative movement of the container and the piston being controlled by said displacement of the fluid,
   wherein said chamber is configured to restrict said displacement of the fluid such that relative movement of the container and the piston is permitted in response to quasi-static changes in pressure, and is prevented in response to vibrational changes corresponding to sound frequencies.

2. The ORP as claimed in claim 1, wherein said fluid is a non-Newtonian fluid.

3. The ORP as claimed in claim 1, wherein said fluid is a dilatant fluid.

4. The ORP as claimed in claim 1, wherein said fluid is a thixotropic fluid.

5. The ORP as claimed in claim 1, wherein said fluid comprises a Newtonian fluid.

6. The ORP as claimed in claim 1, wherein said coupling is adapted to be deformed to permit relative rectilinear motion between first and second attachment points.

7. The ORP as claimed in claim 1, wherein a stiffness of said coupling is variable.

8. The ORP as claimed in claim 1, wherein a stiffness of said coupling is variable in response to variations in the frequency of an applied load.

9. The ORP as claimed in claim 1, wherein a stiffness of said coupling increases in response to an increasing frequency of an applied load.

10. The ORP as claimed in claim 1, wherein a stiffness of said coupling is variable in response to variations in magnitude of an applied load.

11. The ORP as claimed in claim 1, wherein a stiffness of said coupling decreases in response to an increasing magnitude of an applied load.

12. The ORP as claimed in claim 1, wherein said coupling is adapted to exert a pre-load between first and second attachment points.

* * * * *